United States Patent
Sofer et al.

(10) Patent No.: US 10,190,991 B2
(45) Date of Patent: Jan. 29, 2019

(54) METHOD FOR ADAPTIVE SAMPLING IN EXAMINING AN OBJECT AND SYSTEM THEREOF

(71) Applicant: Applied Materials Israel Ltd., Rehovot (IL)

(72) Inventors: Yotam Sofer, Givatayim (IL); Idan Kaizerman, Meitar (IL)

(73) Assignee: Applied Materials Israel LTD., Rehovot (IL)

( * ) Notice: Subject to any disclaimer, the term of this patent is extended or adjusted under 35 U.S.C. 154(b) by 86 days.

(21) Appl. No.: 15/343,090

(22) Filed: Nov. 3, 2016

(65) Prior Publication Data

US 2018/0306728 A1    Oct. 25, 2018

(51) Int. Cl.
  *G01N 21/88*    (2006.01)
  *G01N 21/95*    (2006.01)

(52) U.S. Cl.
  CPC ..... *G01N 21/8851* (2013.01); *G01N 21/9501* (2013.01); *G01N 2021/8858* (2013.01)

(58) Field of Classification Search
  CPC ........... G01N 21/8851; G01N 21/9501; G01N 2021/8854; G01N 2021/8858; G01N 2021/8861; G01N 2021/8864; G01N 2021/8874; G01N 2021/8877; G01N 2021/8887
  See application file for complete search history.

(56) References Cited

U.S. PATENT DOCUMENTS

| | | | |
|---|---|---|---|
| 5,991,699 A * | 11/1999 | Kulkarni | H01L 22/20 257/E21.525 |
| 7,570,796 B2 | 8/2009 | Zafar et al. | |
| 7,756,658 B2 | 7/2010 | Kulkarni et al. | |
| 8,041,104 B2 | 10/2011 | Toyoda et al. | |
| 8,135,204 B1 | 3/2012 | Chen et al. | |
| 8,175,831 B2 | 5/2012 | Izikson et al. | |
| 8,781,781 B2 | 7/2014 | Kulkarni et al. | |
| 8,855,399 B2 | 10/2014 | Goren et al. | |
| 9,286,675 B1 | 3/2016 | Shabtay et al. | |
| 2005/0033528 A1 | 2/2005 | Toth et al. | |
| 2006/0045326 A1 | 3/2006 | Toyoda et al. | |
| 2008/0163140 A1 | 7/2008 | Fouquet et al. | |
| 2008/0250384 A1 | 10/2008 | Duffy et al. | |

(Continued)

*Primary Examiner* — Toan Le
(74) *Attorney, Agent, or Firm* — Lowenstein Sandler LLP

(57) ABSTRACT

Examining an object, comprising: receiving potential defects, each associated with a location; performing first clustering of the potential defects to obtain first and second subsets, the clustering performed such that potential defects in the first subset are denser in a physical area than potential defects in the second subset; automatically assigning first validity probabilities to potential defects in the first and second subsets; selecting for review potential defects from the first and second subsets, according to a third policy, and in accordance with a strategy for combining top elements and randomly selected elements from the merged list; receiving indications for potential defects in part of the potential defect lists, subsequent to potential defects being reviewed; updating the policies in accordance with validation or classification of items in the first and second subsets; and repeating said assigning, selecting, receiving and updating with the updated policies, until a stopping criteria is observed.

20 Claims, 5 Drawing Sheets

(56) References Cited

U.S. PATENT DOCUMENTS

| | | |
|---|---|---|
| 2009/0043527 A1 | 2/2009 | Park et al. |
| 2009/0299681 A1 | 12/2009 | Chen et al. |
| 2010/0296722 A1 | 11/2010 | Liu et al. |
| 2011/0170091 A1 | 7/2011 | Chang et al. |
| 2011/0202298 A1 | 8/2011 | Izikson et al. |
| 2011/0276935 A1 | 11/2011 | Fouquet et al. |
| 2012/0141013 A1 | 6/2012 | Gao et al. |
| 2012/0257039 A1 | 11/2012 | Abe |
| 2013/0035888 A1 | 2/2013 | Kandel et al. |
| 2013/0064442 A1 | 3/2013 | Chang et al. |
| 2013/0163851 A1 | 6/2013 | Dalla-Torre et al. |
| 2013/0216141 A1 | 8/2013 | Ushiba et al. |
| 2013/0278748 A1 | 10/2013 | Nakayama et al. |
| 2013/0310966 A1 | 11/2013 | MacNaughton et al. |
| 2013/0336575 A1 | 12/2013 | Dalla-Torre et al. |
| 2014/0031630 A1 | 1/2014 | Nguyen |
| 2014/0072203 A1 | 3/2014 | Wu et al. |
| 2014/0241610 A1 | 8/2014 | Duffy et al. |
| 2014/0301630 A1 | 10/2014 | Kulkarni et al. |
| 2014/0376801 A1 | 12/2014 | Karsenti et al. |

\* cited by examiner

METHOD FOR ADAPTIVE SAMPLING IN EXAMINING AN OBJECT AND SYSTEM THEREOF

TECHNICAL FIELD

The presently disclosed subject matter relates to examining locations in object, and more particularly to adaptive sampling of object locations to be reviewed.

BACKGROUND

Various objects such as semiconductor wafers, masks, printed circuit boards, solar panels, microelectromechanical devices, are manufactured by manufacturing processes that are highly complex and costly, comprise multiple stages, and require highly accurate machines. Such objects are generally referred to as wafers.

The complex manufacturing process is not error free and such errors can cause faults or alleged faults in the manufactured objects. The faults can include defects that can harm the operation of the object, false positive findings, which may seem to contain a defect although there is no actual defect at the area, and nuisances which may be defects but do not cause any harm or malfunction of the manufactured unit. In addition to faults in the raw material, human errors and others may also cause defects in the objects.

The term "defect" used in this specification should be expansively construed to cover any kind of abnormality or undesirable feature formed on or within a wafer.

The term "examination", unless specifically stated otherwise, used in this specification in a relation to a wafer should be expansively construed to cover any kind of detection and/or classification of defects in the wafer provided by using non-destructive inspection tools. By way of non-limiting example, such examination can include generating one or more recipes for examination and/or parts thereof; inspection, e.g., scanning in a single or in multiple scans; reviewing; measuring and/or other operations provided with regard to the wafer or parts thereof using the same or different inspection tools.

In order to find defects, various examination steps can be integrated into the manufacturing process, including inspection and review. The examination steps can be performed a multiplicity of times, for example at certain stages such as after the manufacturing or processing of certain layers, or the like. Additionally or alternatively, each examination step can be repeated multiple times, for example for different wafer locations or for the same wafer locations with different examination settings.

By way of non-limiting example, examination can employ a two phase "inspection and review" procedure.

The term "inspection" refers to scanning and analyzing a wafer or a part thereof, in order to detect locations in which defects may be found. Suspicious locations reported by an inspection can include true defects, false positive reports, and nuisance defects, which are harmless. A variety of non-destructive inspection tools can be used, which include, by way of non-limiting example, scanning electron microscopes, atomic force microscopes, optical inspection tools, etc.

The term "review" refers to capturing and analyzing one or more specific locations, for example locations of potential defects reported by the inspection process, locations of interest derived from design data, locations indicated by a user, or the like.

The term "design data" used in the specification should be expansively construed to cover any data indicative of hierarchical physical design (layout) of a specimen. Design data can be provided by a respective designer and/or can be derived from the physical design (e.g. through complex simulation, simple geometric and Boolean operations, etc.). Design data can be provided in different formats as, by way of non-limiting examples, GDSII format, OASIS format, etc. Design data can be presented in vector format, grayscale intensity image format or otherwise. Design data comprise design structural elements that represent different features to be formed on one or more layers of a specimen. As known in the contemporary art, a design structural element can be constructed as a geometrical shape with a closed contour or a geometrical shape combined with insertion of other structural elements. By way of non-limiting examples, a given design structural element can comprise one or more STRUCTURE elements inserted by means of SREF, AREF directives in GDSII format, or can comprise one or more CELL elements inserted by means of PLACEMENT and REPETITION (OASIS format).

Typically, inspection is performed at higher speed and lower resolution than review. Thus, inspection can be used for covering larger areas and detecting potential defects, wherein some or all of which can later be reviewed and optionally further examined. During review, some of the potential defects reported by the inspection tool can prove to be false alarms.

In some embodiments, inspection and review can be performed by different tools, but in other embodiments they can be performed by the same tool.

General Description

One aspect of the disclosure relates to a method for examining an object using a processor operatively connected to a memory, the method comprising: receiving a multiplicity of potential defects, each potential defect of the multiplicity of potential defects associated with a potential defect location; performing a first clustering of the multiplicity of potential defects to obtain a first subset and one or more second subsets, the clustering performed in accordance with spatial distances between potential defect locations, such that potential defects in the first subset are characterized by higher density in one or more physical areas than potential defects comprised in the second subsets; automatically assigning first probabilities to be valid defects to potential defects in the first subset, the first probabilities calculated in accordance with a first policy; automatically assigning second probabilities to be valid defects to potential defects in the second subsets, the second probabilities calculated in accordance with a second policy specifying how to combine two or more second factors; automatically selecting and assigning for review by a review tool a potential defect from the first subset and the second subsets, in accordance with a third policy specifying how to combine potential defects from a multiplicity of subsets into a merged list, and in accordance with a strategy indicating how to combine top elements from the merged list and randomly selected elements from the merged list, in accordance with considerations including number of reviews; receiving validity or class indications for potential defects in the part of the potential defect lists, the indications received subsequent to potential defects in the part of the potential defect lists being reviewed by the review tool; and subsequent to a stopping criteria not being observed: updating the first, second, or third policy in accordance with validation or classification of an item in the first subset and the second subsets; and repeating said assigning, selecting, receiving and updating, in accordance with the first, second, or third policy as updated, until the stopping criteria is observed. Within the method, the stopping criteria is optionally selected from the group consisting of: a predetermined number of potential defects have been reviewed by the review tool; convergence of a number of indications that a potential defect is valid; and a predetermined number of defects associated with a specific defect class have been detected. Within the method, a decision confidence level is optionally received for the validity or class indications received. Within the method, a physical area is optionally selected from the group consisting of: a region; an area in the vicinity of an open line; and an area in the vicinity of a close line. The method can further comprise performing a second clustering of the second subset based on characteristics other than geometric location. Within the method, the characteristics of the second clustering optionally include an item selected from the group consisting of: shade or color of the wafer at a location of a potential defect; background shade or color of the wafer at an area of the potential defect; edges in the vicinity of the potential defect; a feature in the vicinity of the potential defect; number of polygons, edges, or corners and density thereof in the vicinity of the potential defect. Within the method, the second clustering optionally provides for determining potential defects located in a dense area in relation to characteristics used for the second clustering, thereby providing for determining systematic potential defects. Within the method, the two or more second factors in respect of the random potential defects are optionally selected from the group consisting of: being located at an area which is sparse in feature space in relation to the characteristics used for the second clustering; being located at an outlier area of an area which is dense in feature space in relation to the characteristics used for the second clustering; proximity to a validated potential defect; and a combination of two or more of the above, thereby providing for determining random potential defects. Within the method, the random potential defects are optionally associated with two or more scans taken by different tools or under different conditions. Within the method, automatically selecting and assigning for review optionally comprises: sorting potential defects of the first subset according to the first probability, to obtain a first sorted list; sorting each of the second subsets according to the second probability, to obtain one or more second sorted lists; prioritizing potential defects from the first sorted list or the second sorted lists to form a merged list, in accordance with the third policy; and selecting potential defects to be reviewed from the merged list in accordance with the strategy. Within the method, the third policy optionally complies with one or more items selected from the group consisting of: selecting a predetermined percentage of a required number of potential defects from the first sorted list and complementing with potential defects from the second sorted lists; selecting top probability potential defects from a merged list of the first sorted list and the second sorted lists, sorted by probability; and prioritizing potential defects from the first sorted list or the second sorted lists in accordance with user input and selecting top priority potential defects. Within the method, the strategy optionally indicates a number of top probability potential defects to be selected from the merged list, and complementing with randomly selected potential defects from the merged list. Within the method, the strategy optionally changes between iterations. Within the method, the strategy optionally changes between iterations in accordance with an item selected from the group consisting of: increasing the number of randomly selected potential defects in advanced iterations relative to earlier iterations; increasing the number of randomly selected potential defects if a number of true defects identified in a previous iteration is below a threshold; increasing the number of randomly selected potential defects if a number of true defects identified in a previous iterations converges; and changing the number of randomly selected potential defects in accordance with type or location distribution of true defects identified in one or more previous iterations. Within the method, assigning the first probabilities or assigning the second probabilities optionally comprises receiving a user indication to assign higher priority to potential defects at specific areas or of specific classes. Within the method, the object is optionally a wafer or a mask.

Another aspect of the disclosure relates to a computerized system comprising a processor configured for: receiving a multiplicity of potential defects, each potential defect of the multiplicity of potential defects associated with a potential defect location; performing a first clustering of the multiplicity of potential defects to obtain a first subset and one or more second subsets, the clustering performed in accordance with spatial distances between potential defect locations, such that potential defects in the first subset are characterized by higher density in a physical area than potential defects comprised in the second subsets; automatically assigning first probabilities to be valid defects to potential defects in the first subset, the first probabilities calculated in accordance with a first policy; automatically assigning second probabilities to be valid defects to potential defects in the second subsets, the second probabilities calculated in accordance with a second policy specifying how to combine two or more second factors; automatically selecting and assigning for review by a review tool one or more potential defects from the first subset and the second subsets, in accordance with a third policy specifying how to combine potential defects from a multiplicity of subsets into a merged list, and in accordance with a strategy indicating how to combine top elements from the merged list and randomly selected elements from the merged list, in accordance with considerations including number of reviews; receiving validity or class indications for potential defects in a part of the potential defect lists, the indications received subsequent to potential defects in the part of the potential defect lists being reviewed by the review tool; and subsequent to a stopping criteria not being observed: updating the first, second, or third policy in accordance with validation or classification of an item in the first subset and the one second subsets; and repeating said assigning, selecting, receiving and updating, in accordance with the first, second, or third policy as updated, until the stopping criteria is observed. Within the system, the stopping criteria is optionally selected from the group consisting of: a predetermined number of potential defects have been reviewed by the review tool; convergence of a number of indications that a potential defect is valid; and a predetermined number of defects associated with a specific defect class have been detected. Within the system, automatically selecting and assigning for review comprises: sorting potential defects of the first subset according to the first probability, to obtain a first sorted list; sorting each of the second subsets according to the second probabilities, to obtain second sorted lists; prioritizing potential defects from the first sorted list or the second sorted lists to form a merged list, in accordance with the third policy; and selecting potential defects to be reviewed from the merged list in accordance with the strategy, and wherein the third policy complies with an item selected from the group consisting of: selecting a predetermined percentage of a required number of potential defects from the first sorted list and complementing with potential defects from the second sorted lists; selecting top probability potential defects from a merged list of the first sorted list and the second sorted lists, sorted by probability; and prioritizing potential defects from the first sorted list or the second sorted lists in accordance with user input and selecting top priority potential defects.

Yet another aspect of the disclosure relates to a computer program product comprising a computer readable storage medium retaining program instructions, which program instructions when read by a processor, cause the processor to perform a method comprising: receiving a multiplicity of potential defects, each potential defect of the multiplicity of potential defects associated with a potential defect location; performing a first clustering of the multiplicity of potential defects to obtain a first subset and one or more second subsets, the clustering performed in accordance with spatial distances between potential defect locations, such that potential defects in the first subset are characterized by higher density in a physical area than potential defects comprised in the second subsets; automatically assigning first probabilities to be valid defects to potential defects in the first subset, the first probabilities calculated in accordance with a first policy; automatically assigning second probabilities to be valid defects to potential defects in the second subsets, the second probabilities calculated in accordance with a second policy specifying how to combine two or more second factors; automatically selecting and assigning for review by a review tool one or more potential defects from the first subset and the second subsets, in accordance with a third policy specifying how to combine potential defects from a multiplicity of subsets into a merged list, and in accordance with a strategy indicating how to combine top elements from the merged list and randomly selected elements from the merged list, in accordance with considerations including number of reviews; receiving validity or class indications for potential defects in a part of the potential defect lists, the indications received subsequent to potential defects in the part of the potential defect lists being reviewed by the review tool; and subsequent to a stopping criteria not being observed: updating the first, second, or third policy in accordance with validation or classification of an item in the first subset and the second subsets; and repeating said assigning, selecting, receiving and updating, in accordance with the first, second, or third policy as updated, until the stopping criteria is observed.

BRIEF DESCRIPTION OF THE DRAWINGS

In order to understand the invention and to see how it can be carried out in practice, embodiments will be described, by way of non-limiting examples, with reference to the accompanying drawings, in which.

DETAILED DESCRIPTION

Figure 1A:
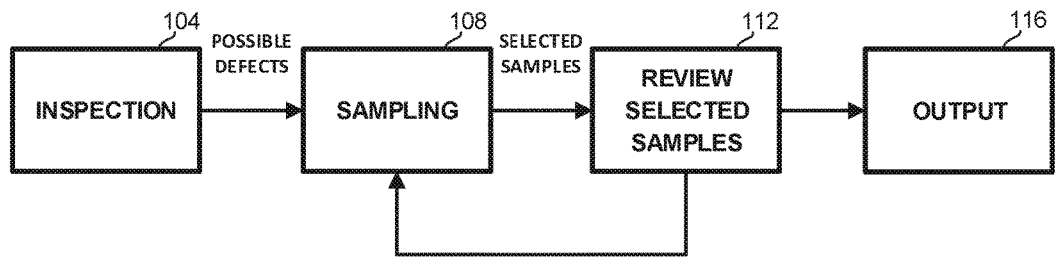
FIG. 1A illustrates a prior art generalized flowchart of an examination process of a wafer.

In the following detailed description, numerous specific details are set forth in order to provide a thorough understanding of the invention. However, it will be understood by those skilled in the art that the presently disclosed subject matter can be practiced without these specific details. In other instances, well-known methods, procedures, components and circuits have not been described in detail so as not to obscure the presently disclosed subject matter.

Unless specifically stated otherwise, as apparent from the following discussions, it is appreciated that throughout the specification discussions utilizing terms such as "processing", "computing", "representing", "comparing", "generating", "assessing", "matching", "updating" or the like, refer to the action(s) and/or process(es) of a computer that manipulate and/or transform data into other data, said data represented as physical, such as electronic, quantities and/or said data representing the physical objects. The term "computer" should be expansively construed to cover any kind of hardware-based electronic device with data processing capabilities.

The operations in accordance with the teachings herein can be performed by a computer specially constructed for the desired purposes or by a general-purpose computer specially configured for the desired purpose by a computer program stored in a non-transitory computer-readable storage medium.

The terms "non-transitory memory" and "non-transitory storage medium" as used herein should be expansively construed to cover any include any volatile or non-volatile computer memory suitable to the presently disclosed subject matter.

The term "review location" used herein should be expansively construed to cover any location on an object, such as a wafer, a mask, a printed circuit board, a solar panel, a microelectromechanical device, or the like, required to be reviewed. A location can relate to a point, expressed as a set of coordinates in two or three dimensions, or to a line or two- or three-dimensional area, depending on the context. Review locations can be associated with revealed or potential defects, patterns of interest (e.g. crossing of specific design elements), or otherwise defined regions of interest determined during one or more examination stages, for example detected during inspection by taking one or more optical images of the wafer or part thereof, and comparing an obtained image or features therein to an expected image or to predetermined features, wherein the differences can be regarded as potential defects. The review locations can further include any other locations it can be required to review, which can be provided automatically, manually, provided by a user, or the like. A review location can be specified in design coordinates and/or coordinates tied to a wafer or parts thereof.

The term "Automatic Defect Classification" (ADC) refers to an optional stage which can be performed as part of reviewing a possible defect, for determining a class with which a potential defect can be associated, for example: a false defect (false alarm); a nuisance which can be a defect that does not cause any harm or malfunction of the manufactured unit, or a real defect. The real defects can also be classified into a multiplicity of classes, in accordance with a number of types or parameters, such as but not limited to different particle composition or sizes; different void size or location within an object; an electrical short or an electrical open; a macro or micro scratch; unremoved material; extra material; misaligned features; pattern masking, or others.

In some embodiments, true defects can be assigned with priority which reflects their importance to the user.

The term "sampling" used herein should be expansively construed to cover any selection of one or more wafer locations, from a collection of wafer locations obtained by an inspection tool or from any other source, for example received from a user, extracted from design data, reported by from previous processes, received from external sources, or others. The sampled wafer locations can be selected from amongst the collection of wafer locations, to be reviewed by a review tool.

Reference is now made to FIG. 1A, showing a schematic flowchart of a prior art process for examining a wafer.

At step 104, an inspection device of a system, such as the system described in association with FIG. 2 below, inspects the wafer. As detailed above, the inspection process can cover a large area at low resolution, and can thus provide a multiplicity of wafer locations, each of which may or may not be a location of a true defect in the wafer. The inspection tool is operative in covering a large area of the wafer at significant speed, at a price of significant false alarm rate. Due to the large number of potential defects and the high false alarm rate, it may be impossible to review all the potential defects in order to verify which are indeed true defects and which are not, and to classify them. For example, as the design rule shrinks and the complexity of pattern increases, the false alarm rate can exceed 99 percent.

Therefore, at step 108 the system can perform sampling for selecting a subset of the potential defects to be reviewed, for example by a slower but higher-resolution review device.

At step 112 a review device of the system can review the selected samples. Optionally, the review results, for example images taken by a capture device, can also be reviewed by a user or another process, for verifying whether the reviewed location is indeed associated with a true defect, or for classifying the defect.

Sampling step 108 can then be repeated, for example until a predetermined number of true defects is determined, until manufacturing schedule or lack of other resources do not allow any more reviews.

The system can output the review results at step 116, for example displaying or sending to a user or to a process, store in a file or a database, or the like.

Figure 1B:
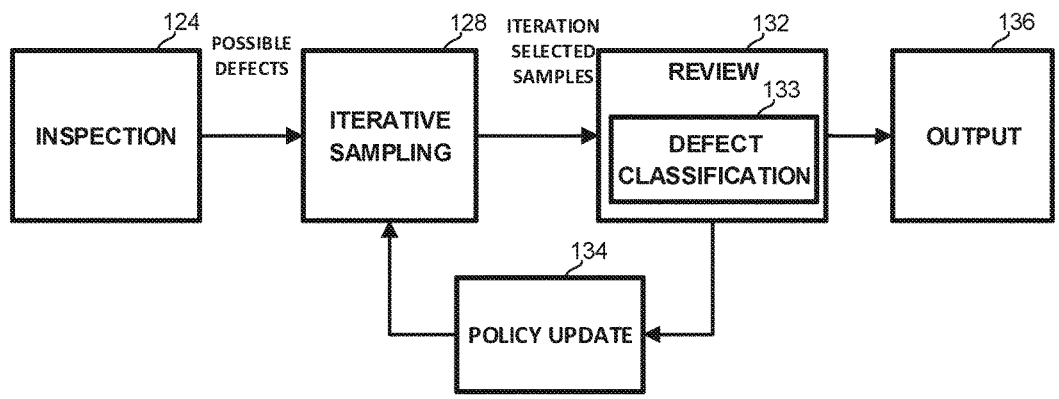
FIG. 1B illustrates a generalized flowchart of an examination process of a wafer, in accordance with some exemplary embodiments of the disclosure.

Reference is now made to FIG. 1B, showing a schematic flowchart of a process of examination, in accordance with some embodiments of the disclosure.

At step 124 an inspection device of an examination system can inspect the wafer or part thereof as detailed in association with step 104 above, and potential defects can be determined. Each such potential defect can be associated with a location and optionally with characteristics, expressed for example as a vector of features.

At step 128 the system can perform iterative sampling, in which a subset of the potential defects is selected at each iteration to provide iteration selected samples. The iterative sampling can be performed in accordance with one or more policies, related for example to how to prioritize and sample the wafer locations, as detailed below.

At step 132 a review device can review the iteration selected samples as detailed in association with step 112 above.

Step 132 can comprise step 133 for classification of the defects into predetermined classes. Step 133 can be performed as part of step 132, or as a separate step.

At step 134, the system can update the sampling policies in accordance with the review results, or can feed back the updated policy, and can perform again iterative sampling step 128 in accordance with the results or with the updated policies.

At step 136 the system can output the results of the last iteration and optionally previous iterations as detailed in association with step 116 above.

Figure 2:
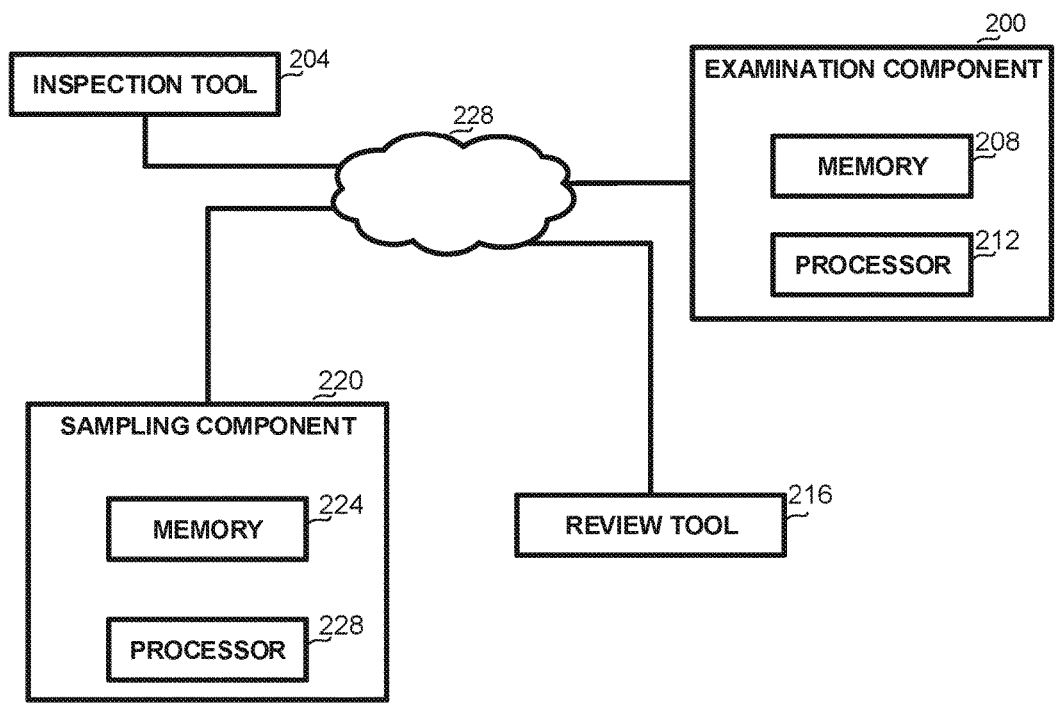
FIG. 2 illustrates a generalized block diagram of systems for examining a wafer in accordance with some exemplary embodiments of the disclosure.

Reference is now made to FIG. 2, showing a schematic diagram of a computerized environment for examining a wafer, in accordance with some embodiments of the disclosure.

FIG. 2 illustrates examination component 200, inspection tool 204, review tool 216, and sampling component 220.

A network 228 is coupled to examination component 200, inspection tool 204, review tool 216, and sampling component 220. For example, network 228 can be a fab communication system. For simplifying the explanation, only a single inspection tool 204 and a single review tool 216 are shown. However, it should be noted that in practice, a plurality of inspection tools and a plurality of review tools can be used and connected via network 228. For further simplifying the explanation, a single sampling component 220 and a single examination component 200 are shown. It should be noted, however, that more than one sampling component 220 or more than one examination component 200 can be used. Additionally or alternatively, each of sampling component 220 and examination component 200 can be implemented as one or more interconnected computing platforms.

The invention is not limited by the type of physical communication and coupling provided between the various entities of FIG. 2. Any two components can be connected directly, via network 228, via any other component, whether such component is shown in FIG. 2 or not.

Although, for simplifying the explanation, sampling component 220 and examination component 200 are shown as stand-alone computer systems, it is noted that any of these can be a part of inspection tool 204 or of review tool 216. Alternatively, sampling component 220 and examination component 200 can be implemented as one computer system. According to some embodiments of the invention, one or more of sampling component 220 and examination component 200 can be facilitated as a hardware utility which is placed on an electronic rack of, for example, inspection tool 204, review tool 216 or any other computing system associated with the fab.

Examination component 200 can be configured to execute the method of FIG. 1B (including activating sampling component 220) above, and sampling component 220 can be configured to execute the method of FIG. 3 and FIG. 4 below.

Sampling component 220 can include a memory unit 224 and a processor 228.

Memory unit 224 can be configured to store at least one of: information required for executing a method such as the method detailed in FIG. 3 below; software required for executing said method; or information generated during the execution of said method.

Processor 228 can be configured to perform any operation required during any step of a method such as the method detailed in FIG. 3 below.

Examination component 200 can include a memory unit 208 and a processor 212.

Memory unit 208 can be configured to store at least one of: information required for executing the method depicted in FIG. 1B above; software required for executing said method; or information generated during the execution of said method.

Processor 212 can be configured to perform any operation required during any step of the methods depicted in FIG. 1B above.

It will be appreciated that the examination process depicted in FIG. 2 can be repeated multiple times, for different layers, or different parts of the wafer, different stages on the manufacturing process, or the like.

Examination component 200 can be configured to activate sampling component 220 for iteratively sampling (128) those defects that will be reviewed (132), out of the potential defects received from the inspection (124).

Figure 3:
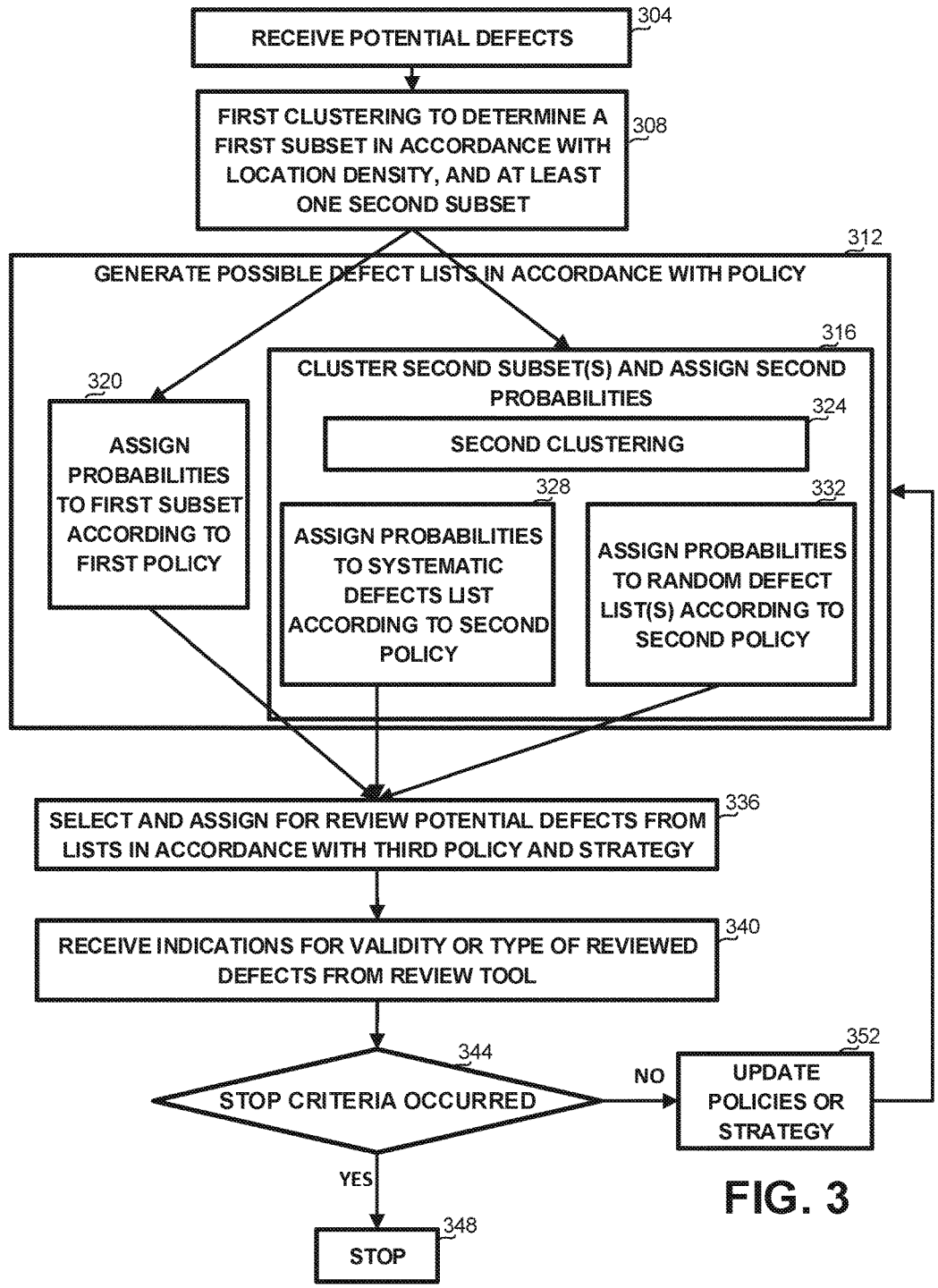
FIG. 3 illustrates an exemplary flowchart of the sampling and review process of a wafer, in accordance with some exemplary embodiments of the disclosure.

Reference is now made to FIG. 3, showing a flowchart of a method of iterative sampling of potential defects during examination.

Processor 220 of sampling component 228 can perform iterative sampling step 128.

Iterative sampling step 128 can include step 304 of obtaining and accommodating in memory a plurality of potential defects. The potential defects, for example potential defects detected by inspection step 124, potential defects obtained from analyzing design data of the wafer, or from any other source. The potential defects can be received from a storage device, from a user, from a third party or any other external source. Each potential defect can be associated with a location or with a characteristic which can be expressed as a vector of features.

Processor 220 can obtain the potential defects from one or more scan sets, wherein two scan sets can differ in the inspection tool used for taking them, detection sensitivity thresholds or in any of the imaging parameters of the scanning, such as magnification, light direction and wave length, light power, polarization, light collecting angle, or the like.

Sampling component 220 can be configured to perform step 308, in which the potential defects are clustered on a first clustering step to determine a first cluster and at least one second cluster. The first clustering can utilize the location of the defects and can be based on the spatial distances between defects. The first cluster can be referred to as comprising "signature" defects, which can be characterized by high density of defects within an area, along a radial area of the wafer, along a perimeter of an area partial to the wafer, along an open line, or by any other geometric characteristic.

The signature defects can be caused by a careless touch of the wafer, a scratch, or the like.

Signature defects can be determined by clustering the defects in accordance with a geometric metric, such that defects that are physically close to each other are likely to be associated with the same cluster, while distant defects are likely to be clustered into different clusters. Clustering step 308 can utilize the K-means, hierarchical clustering, mean shift or any other clustering algorithm.

Thus, the first subset can comprise a multiplicity of potential defects assumed to be associated with an area. It will be appreciated that a multiplicity of first subsets can be determined by the clustering, wherein which subset can be attributed to the same area or cause, such as a scratch.

Potential defects not associated with the first subset that are associated with the same second subset can be attributed to geometric proximity, but can be not as close to each other as potential defects in the first subset(s).

It will be appreciated that clustering step 318 can take place separately for the potential defects provided by each scan set. Alternatively, potential defects stemming from different scan sets can be clustered together, in which case multiple entries in one or more clusters can refer to the same potential defect.

Iterative sampling component 220 can perform step 312 of generating potential defect lists in accordance with one or more policies.

Iterative sampling component 220 can perform step 320, which can be a part of step 312, of assigning probabilities to potential defects in the first subset(s) in accordance with a first policy. It will be appreciated that in the description below, the term probability relates to an estimation of the probability that a potential defect is a true defect.

The first policy, which relates to signature potential defect, can be assigned based on a number of probabilities, such as but not limited to the following:

1. Signature types: signature defects can be classified into categories based on parameters such as size, density, shape and location on the wafer. Some signature categories have known probability of being proven to be true defects, thus defects belonging to such types can be assigned predetermined probabilities.

2. Label homogeneity: labels relate to a defect being classified as true or false. Signature defects tend to contain defects of similar labels, so if a portion of defects from a signature are proven to be true, then most of the defects in the signature can be assumed to be true as well, and similarly for false defects. In both cases, reviewing further defects of the same signature can be less important since there is high confidence on whether they are true or false. If various types of defects are present, further sampling can be required.

3. Specific defects in the signatures are sampled based on outlier detection together with measures discussed above. If the signature is homogeneous then sampling can be based on outlier detection, in order to further identify types of defects in the signature. The policy can dictate, for example, that a potential defect that is closer to the center of a hypersphere of the potential defects associated with each cluster is assigned lower probability than peripheral potential defects. Alternatively, a defect whose sum of geometric or Euclidean distance from other defects in the same cluster is larger than the distance sum of its neighboring defects, can be assigned higher probability. In further alternatives, any other outlier detection criteria can be used by the policy for estimating the probability. The probability can increase as the distance of the potential defect from known true defects decreases, wherein distance can be measured in the feature space of the defect characteristics. If a signature is highly homogenous, it can be beneficial to assign higher probabilities to outlier defects which may contain new information, otherwise random sampling of the signature defects may be preferred.

The three probabilities discussed above can be combined into a single probability, for example by a linear combination. It will be appreciated that while the probabilities of specific defects, as detailed in the third item above, are constant and relate to their location in feature space, the label homogeneity and signature types probabilities, detailed in the first and second items above, can be updated upon feedback from the results of previous classifications. The signature type can be used as a basis for a-priori probability, based on the confidence of the classifier related to each type. The first probability can be updated based on the received label indications and their correlation to specific signature types.

Iterative sampling component 220 can perform step 316 which can be a part of step 312, of assigning probabilities to potential defects in the second subset.

Step 316 can include second clustering step 324 of the potential defects in the second subset(s). The second clustering can use one or more metrics other than the geometric ones, which were used in clustering step 308. For example, a metric based on any one or more of the following can be used: shade, color, shape or size of the area of the potential defect; the area shade or color relative to the background or properties of gray level distribution; context attributes, such as edges or their density, typical amplitude or distribution of the directions of the edges directions in the vicinity of the potential defect or other features in the vicinity of the potential defect, which can be expressed using a Fourier transform or another function of the image edges or other features; design attributes, such as the number of polygons, length of perimeter, number of various corners and density or other features in the vicinity of the potential defect, which can be expressed using a Fourier transform or another function of the polygons, edges, corners or other features, or the like.

It will be appreciated that second clustering step 324 can include two or more clustering operations, based on different sets of attributes or different metrics.

For example, one or more clusters can be attributed to density in the space of characteristics associated with the design, such as the edges or polygons in the vicinity of the potential defects. Thus, potential defects assigned to the same cluster can be attributed to the design and can be referred to as "systematic" potential defects. For example, some design features may not be captured well by the inspection tool, and can generate a multiplicity of systematic potential defects, which are actually false alarms.

Thus, in some embodiments, clustering can be performed with design attributes as detailed above, and one or more clusters of potential defects which are dense in regard to these attributes can be determined. The rest of the potential defects, referred to as "random" potential defects, can undergo further clustering, using different characteristics or metrics In the description below, the terms distance, density, sparsity, close, distant or others, relate to the metric used during clustering, rather than to geometric distance.

Iterative sampling component 220 can perform step 328, which can be a part of step 312, of assigning probabilities to systematic defects, which can be associated with design problems, in accordance with a second policy.

The probability can be set, for example, based on parameters such as label homogeneity and outlier degree, as detailed in parameters 2 and 3 in the description related to assigning probability to signature defects above.

Iterative sampling component 220 can perform step 332, which can be a part of step 312, of assigning probabilities to random defects, in accordance with the second policy, wherein the assigned value is an estimated probability of the random potential defect to be a true defect.

It will be appreciated that the second policy can comprise separate sub-policies for assigning probabilities to systematic (step 328) and to random defects (step 332). Alternatively, two separate policies can be used.

The second policy can assign probabilities to the random potential defects at step 332 based on one or more factors, which can include but are not limited to any one or more of the following criteria.

1. Being located at an N-dimensional sparse area, wherein the dimensions can relate to any parameter of the defect, but preferably not to its location which is considered in first clustering step 308. Since in current technologies most potential defects are proven to be false alarms rather than true defects, a dense area can represent noise more than it represents true defects. Therefore potential defects located in N-dimensional sparse areas can be more likely to be true defects;

2. Being an outlier, i.e., be located on the margins of a dense area: a defect whose sum of distances from other defects in its neighborhood is larger than the corresponding sum of its neighbors, can be assigned a higher probability than other defects. In further alternatives, any other outlier detection criteria can be used for estimating the probability; or 3. Proximity to a known true defect, to a known defect of particular interest, or to an area of interest indicated by a user: if a potential defect has been sampled in a previous iteration and is proven to be a true defect or defect of a particular interesting type, then defects which are close to it can be assumed to be true defects as well.

The specific factors selected and their relative weights can be determined by the second policy and can change between iterations.

Thus, the output of step 312 can comprise zero, one or more collections of signature potential defects; zero, one or more collections of systematic potential defects; and zero, one or more collections of random potential defects, each potential defect of any of the collections associated with a probability to be a valid defect.

It will be appreciated that there can be repetitions within any of the subsets, or between different subsets, for example due to potential defects reported in more than one scan set. Since clustering can be a heuristic process, one instance of a potential defect can be identified as a systematic defect, while another instance of the same defect can be identified as a random potential defect.

Iterative sampling component 220 can be configured to perform step 336, in which potential defects from subsets of the types described above are sorted in accordance with a third policy and are selected for review in accordance with a strategy.

Figure 4:
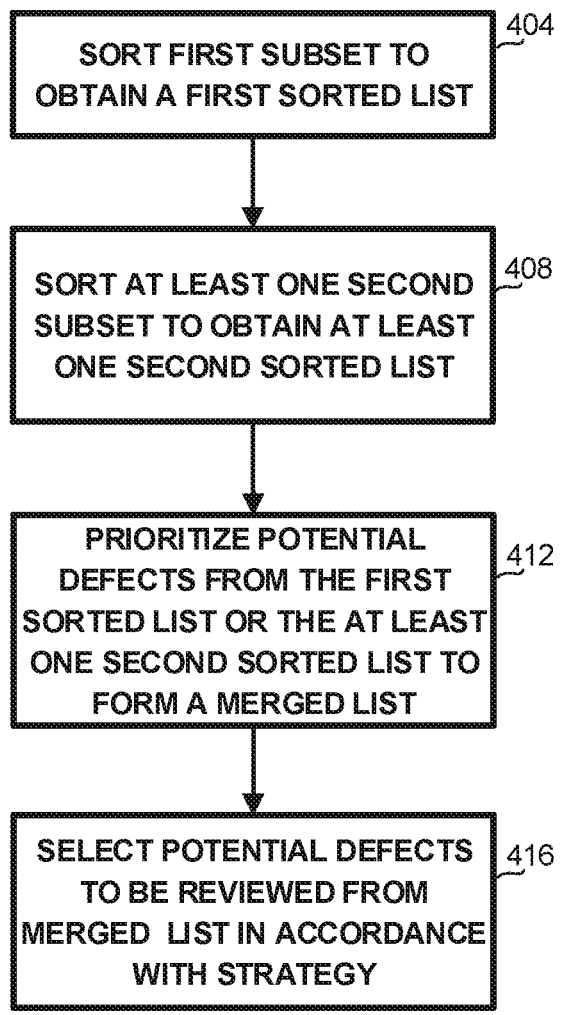
FIG. 4 illustrates an exemplary flowchart of selecting samples from multiple subsets for review, in accordance with some exemplary embodiments of the disclosure.

Reference is now made to FIG. 4, showing a flowchart of an embodiment of a method of selecting and assigning potential defects for review, thus detailing step 336 above.

At step 404, iterative sampling component 220 can sort potential defects of the first subset, e.g., signature defects in accordance with the assigned probability. If multiple first subsets exist, each can be sorted in accordance with the probabilities assigned to potential defects in the specific subset. Alternatively, all first subsets can be merged and sorted into a first sorted list.

At step 408, iterative sampling component 220 can sort potential defects of the second subsets, including one or more subsets of systematic defects or one or more subsets of random defects in accordance with the assigned probability, into one or more second sorted lists. Each of the systematic subsets and the random subsets can be sorted in accordance with the probabilities assigned to potential defects in the specific subset. Alternatively, all second subsets can be merged and sorted into a second sorted list. In yet another alternative, all systematic defect subsets can be merged and sorted, or all random defect subsets can be merged and sorted.

At step 412, iterative sampling component 220 can prioritize potential defects from the first or the second sorted lists to form a merged list of potential defects to be reviewed by review tool 216.

The potential defects to be reviewed can be selected in accordance with a third policy which can change between iterations. The policy can change in accordance with the needs, the review budget, results of previous iterations related to number and ratio of true/false defects or to classification thereof, user preferences, or the like.

For example, any one or more of the following policies can be employed for merging the lists:

Taking an equal number of potential defects from each sorted list. Thus, if there is a budget of 100 potential defects to be reviewed and four lists, the 25 potential defects having the highest probabilities from each list can be selected for review;

Taking the potential defects having the highest probabilities from all lists together, which is equivalent to merging the lists, sorting the merged list and selecting the highest prioritized potential defects;

Sampling from each subset a number of potential defects relative to the subset size. For example, if one subset is twice as long as another one, then the number of samples from this subset will be twice the number of samples from the other one, wherein from each subset the potential defects with the highest probability will be selected;

Assigning a weight to each scan set and multiplying or otherwise combining the probability of each potential defect with the weight of the scan set by which it was reported, and then selecting potential defects in accordance with the weight probability using any of methods 1-3 above. The weight can be adjusted between iterations: for example a list associated with a scan set in which the percentage of true defects is higher than others can be assigned a higher weight for the next one or more iterations.

Selecting in accordance with user input. For example, if a user is interested in a specific area of the wafer, potential defects in this area will be selected before potential defects in other areas. If the user is interested in a specific type of potential defects, such as potential defects in bridges, such information can be obtained from the design data and thus such potential defects are likely to appear in the systematic defect subsets, therefore potential systematic defects can be selected prior to other ones.

It will be appreciated that many other policies can be employed for combining the subsets, thus forming a merged list ordered by the probability of the potential defects.

The merged list can be longer than the number of potential defects that can be reviewed in the current iteration.

Therefore, at step 416, iterative sampling component 220 can select potential defects to be reviewed from the merged list, in accordance with a strategy. It will be appreciated that the number of potential defects to be selected on each iteration can depend on the number of total potential defects to be reviewed, and also on the system resources. For example, if review is performed by a single computerized platform, and a multiplicity, for example one hundred cores are available, then it would be reasonable to select a hundred potential defects per iteration, so as to fully utilize the cores.

In some embodiments, the top probability elements can be selected, since they have the highest probability to be true defects. This strategy can be referred to as exploitation, i.e. attempting to obtain as many true defects as possible in accordance with the probability to indeed detect true defects. However, especially in advanced iterations, when the number of new true defects identified in each iteration drops, it can be assumed that the strategy should change, and random potential defects can be selected, regardless of their location in the list. This strategy can be referred to as exploration, i.e., exploring other areas or types of potential defects, without a very strong indication to do so.

It will be appreciated that a combined strategy can be taken, wherein some of the budget of the potential defects to be reviewed is selected to be the potential defects with the highest probability from the merged list, while the rest of the defects can be selected randomly from the merged list. The proportion between the two types, i.e., what percentage or number of the potential defects are selected in accordance with top probabilities, and what percentage or number is selected randomly from the list, can change over time, wherein, in early iterations, all or most of the potential defects can be selected from the top probability ones, and as the iterations advance, more potential defects are selected randomly.

The selection strategy can also change depending on the results of previous iterations. For example, if a significant number of the potential defects were selected by way of exploitation, and a small number, for example a number below a threshold of new defects have been detected, the exploitation percentage can be reduced and more potential defects can be selected randomly; the number of randomly selected potential defects can change in accordance with type or location distribution of true defects identified in one or more previous iteration, or any other one or more factors. The proportion $p_i$ between exploration and exploitation at iteration i can be formulated as $p_i = a \cdot f(i) + b \cdot g(r_{i-n})$ where a and b are linear factors; f is a function reflecting the change between exploration and exploitation of iteration I; r is the ratio of true and false defects in a previous iteration n, wherein n is a user selected parameter between 0 and i−1, for example the first iteration, or the like; and g reflects the change in proportion as a function of the change in true to false ratio, for example g can be an exponential or linear function. Strategies and various actions throughout the iterations can be also defined by Markov Decision Process or learned by Q learning or reinforcement learning approaches.

The locations of the selected potential defects can then be provided to a review tool which can review them, for example, by capturing images. The images can be processed automatically or reviewed by a user, and an indication of whether a reviewed potential defect is a true defect, and optionally its type, for example a bridge, a crossing, particle, residue materials, or an opening, can be provided.

Referring now back to FIG. 3, at step 340 sampling component 220 can obtain information regarding the validity of potential defects, i.e. whether the potential defects are true defects or not, and optionally their type. Optionally, a confidence level can be associated with the indication whether each potential defect is true or false.

Sampling component 220 can then determine at step 344 whether a stop criteria has been met. The stop criteria can be but is not limited to any one or more of the following:

A review budget has been used, i.e., the number of reviews allotted for the wafer or for the examination has been met;

Convergence: whether a sufficient number of true defects have been detected in the previous iterations. For example, if the number of true defects found in the last iteration or the last predetermined number of iterations is below a predetermined threshold consistently over several iterations, then performing further iterations may not be beneficial and the process can be stopped. Alternatively, as mentioned above, in future iterations, a larger percentage of potential defects can be selected randomly and not from the top probability potential defects;

A number of defects associated with a specific defect class have been detected.

If the stop criteria have been observed, the process can end at step 348. However, if the stop criteria have not been met, then at step 352 one or more of the used policies or strategy can be updated. For example, the relative weights used when determining the probability of a systematic or random potential defects can be changed, the manner in which the lists are merged and how potential defects are selected from the merged list can be changed, or the like. The changes can be provided automatically, by a user, or in combination thereof, wherein a policy is suggested automatically and a user can accept or change it.

In some embodiments, further changes can be introduced between iterations. For example, step 328 can be performed using a classifier adjusted for a small number of labels such as K nearest neighbors, but every predetermined number of iterations, or when a condition occurs, such as too many or too few defects of a certain type, a different classification algorithm can be used, such as Support Vector Machine (SVM).

Figure 5:
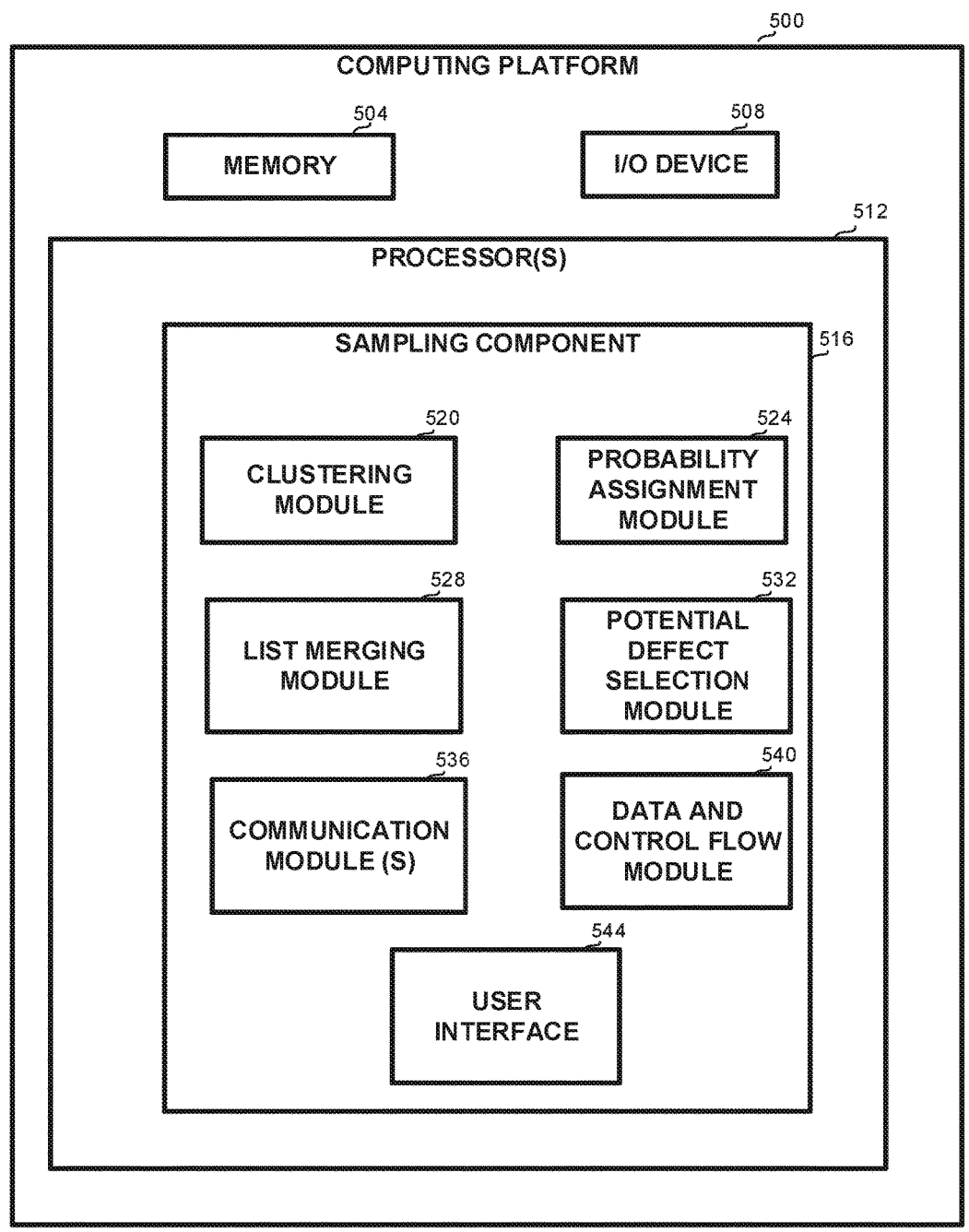
FIG. 5 shows a schematic block diagram of a system for sampling review locations, in accordance with some exemplary embodiments of the disclosure.

Reference is now made to FIG. 5, illustrating a functional diagram of a system for adaptive sampling of location to be reviewed when examining a wafer, in accordance with some embodiments of the disclosure.

The illustrated system can comprise a computing platform 500, implementing sampling component 220 and configured to execute the methods of FIG. 3 and FIG. 4.

Computing platform 500 can comprise a storage device 504. Storage device 504 can be a hard disk drive, a Flash disk, a Random Access Memory (RAM), a memory chip, or the like. In some exemplary embodiments, storage device 504 can retain program code operative to cause processor 512 to perform acts associated with any of the subcomponents of computing platform 500.

In some exemplary embodiments of the disclosed subject matter, computing platform 500 can comprise an Input/Output (I/O) device 508 such as a display, a pointing device, a keyboard, a touch screen, or the like. I/O device 508 can be utilized to provide output to and receive input from a user.

Computing platform 500 can comprise one or more processor(s) 512. Processor 512 can be a Central Processing Unit (CPU), a microprocessor, an electronic circuit, an Integrated Circuit (IC) or the like. Processor 512 can be utilized to perform computations required by computing platform 500 or any of it subcomponents, such as steps of the method of FIG. 3 and FIG. 4.

It will be appreciated that processor 512 can be configured to execute several functional modules in accordance with computer-readable instructions implemented on a non-transitory computer-readable storage medium. Such functional modules are referred to hereinafter as comprised in the processor.

The components detailed below can be implemented as one or more sets of interrelated computer instructions, executed for example by processor 504 or by another processor. The components can be arranged as one or more executable files, dynamic libraries, static libraries, methods, functions, services, or the like, programmed in any programming language and under any computing environment. The components can be loaded to memory and executed.

Processor 512 can be configured to comprise clustering module 520 for clustering a multiplicity of items in accordance with a given metrics. Clustering module 520 can be operative in performing the first clustering of the provided potential defects using a geometrical metrics and clustering them into signature defects and others. Clustering module 520 can also be operative in performing the second clustering of the non-signature defects into further clusters, using other, non-geometric metrics as disclosed above.

Processor 512 can be configured to comprise probability assignment module 524 for assigning a probability to one or more potential defects, based on a policy. The policy can relate to various factors, such as whether it is located in a dense area, regardless of what metric the density is based on, user commands, or others.

Processor 512 can be configured to comprise list merging module 528 for merging two or more lists, wherein each list is ordered with an internal order. The lists can be merged based on any policy, as detailed in association with step 412 of FIG. 4 above.

Processor 512 can be configured to comprise potential defect selection module 532 for selecting potential defects to be reviewed from a merged list. Selection can be made to conform to exploration or exploitation requirements, or a combination thereof, as detailed in association with step 416 of FIG. 4 above.

Processor 512 can be configured to comprise one or more communicating components 536 for communication with other devices, such as inspection or review tools, capture devices, databases, or the like.

Processor 512 can be configured to comprise data and control flow module 540 activating other modules or components at a required stage with the required data or by providing access to such data.

Processor 512 can be configured to comprise user interface 544 for receiving input from a user or providing output to a user, such as indications of defects or areas of interest, exploration/exploitation preferences, or the like. User interface 544 can exchange information with a user by utilizing I/O device 508.

It is noted that the teachings of the presently disclosed subject matter are not bound by the computing platform described with reference to FIG. 5. Equivalent and/or modified functionality can be consolidated or divided in another manner and can be implemented in any appropriate combination of software with firmware and/or hardware and executed on one or more suitable devices.

The system can be a standalone entity, or integrated, fully or partly, with other entities, which can be directly connected thereto or via a network.

It is also noted that whilst the method of FIG. 3 and FIG. 4 can be performed by the system of FIG. 5, this is by no means binding, and the operations can be performed by elements other than those described herein, in different combinations, or the like. It is also noted that the teachings of the presently disclosed subject matter are not bound by the flow charts illustrated in FIG. 3 and FIG. 4, and the illustrated operations can occur out of the illustrated order.

It is to be understood that the invention is not limited in its application to the details set forth in the description contained herein or illustrated in the drawings. The invention is capable of other embodiments and of being practiced and carried out in various ways. Hence, it is to be understood that the phraseology and terminology employed herein are for the purpose of description and should not be regarded as limiting. As such, those skilled in the art will appreciate that the conception upon which this disclosure is based can readily be utilized as a basis for designing other structures, methods, and systems for carrying out the several purposes of the presently disclosed subject matter.

It will also be understood that the system according to the invention can be, at least partly, implemented on a suitably programmed computer. Likewise, the invention contemplates a computer program being readable by a computer for executing the method of the invention. The invention further contemplates a non-transitory computer-readable memory tangibly embodying a program of instructions executable by the computer for executing the method of the invention.

Those skilled in the art will readily appreciate that various modifications and changes can be applied to the embodiments of the invention as hereinbefore described without departing from its scope, defined in and by the appended claims.

The invention claimed is:

1. A method of examining an object, the method comprising:
   (a) identifying, by a processor, a plurality of potential defects, each potential defect of the plurality of potential defects being associated with a potential defect location;
   (b) performing, by the processor, a first clustering of the plurality of potential defects to obtain a first subset and one or more second subsets, the clustering performed in accordance with spatial distances between potential defect locations such that potential defects in the first subset are characterized by higher density in at least one physical area than potential defects in the one or more second subsets;
   (c) assigning, by the processor, first probabilities to potential defects in the first subset to be valid defects, the first probabilities being calculated in accordance with a first policy;
   (d) assigning, by the processor, second probabilities to potential defects in the one or more second subsets to be valid defects, the second probabilities being calculated in accordance with one or more second policies specifying how to combine at least two second factors associated with potential defect locations;
   (e) selecting, by the processor, at least one potential defect from the first subset and the one or more second subsets for review by a review tool in accordance with a third policy specifying how to combine potential defects from a plurality of subsets into a merged list, and wherein the selecting of the at least one potential defect for review by the review tool is further in accordance with a strategy indicating how to combine top elements from the merged list and randomly selected elements from the merged list in accordance with a number of reviews from the review tool;
   (f) receiving, by the processor, validity or class indications for potential defects in a potential defect lists associated with the selected at least one potential defect, the validity or class indications being received subsequent to potential defects in the potential defect lists being reviewed by the review tool; and
   (g) subsequent to a stopping criteria not being observed:
      (i) updating, by the processor, the first, second, or third policy in accordance with validation or classification of an item in the first subset and the one or more second subsets; and
      (ii) repeating, by the processor, steps (c)-(g) in accordance with the first, second, or third policy as updated, until the stopping criteria is observed.

2. The method of claim 1, wherein the stopping criteria is selected from at least one of: a predetermined number of potential defects being reviewed by the review tool, convergence of a number of indications that a potential defect is valid and a predetermined number of defects associated with a specific defect class being detected.

3. The method of claim 1, wherein a decision confidence level is received for at least one of the validity or class indications.

4. The method of claim 1, wherein the at least one physical area is selected from at least one of: a region, an area in the vicinity of an open line, and an area in the vicinity of a closed line.

5. The method of claim 1, further comprising:
   performing a second clustering of the one or more second subsets set based on characteristics other than geometric location.

6. The method of claim 5, wherein the characteristics of the second clustering include at least one item selected from: shade or color of a wafer at a location of a potential defect, background shade or color of the wafer at an area of the potential defect, edges in the vicinity of the potential defect, a feature in the vicinity of the potential defect, number of polygons, edges, or corners and density thereof in the vicinity of the potential defect.

7. The method of claim 5, wherein the second clustering provides for determining potential defects located in a dense area in relation to characteristics used for the second clustering, thereby providing for determining systematic potential defects.

8. The method of claim 5, wherein the at least two second factors are selected from at least one of:
   being located at an area which is sparse in feature space in relation to the characteristics used for the second clustering;
   being located at an outlier area of an area which is dense in feature space in relation to the characteristics used for the second clustering;
   proximity to a validated potential defect; and
   a combination of two or more of the above,
   thereby providing for determining random potential defects.

9. The method of claim 8, wherein the random potential defects are associated with at least two scans taken by different tools or under different conditions.

10. The method of claim 1, wherein
    selecting for review comprises:
    sorting potential defects of the first subset according to at least one first probability to obtain a first sorted list;
    sorting the one or more second subsets according to at least one second probability to obtain at least one second sorted list;
    prioritizing potential defects from the first sorted list or the second sorted list to form a merged list in accordance with the third policy; and
    selecting potential defects to be reviewed from the merged list in accordance with the strategy.

11. The method of claim 10, wherein the third policy complies with at least one item selected from at least one of:
    selecting a predetermined percentage of a required number of potential defects from the first sorted list and complementing with potential defects from the second sorted list;
    selecting top probability potential defects from a merged list of the first sorted list and the second sorted list, sorted by probability; and prioritizing potential defects from the first sorted list or the second sorted list in accordance with user input and selecting top priority potential defects.

12. The method of claim 10, wherein the strategy indicates a number of top probability potential defects to be selected from the merged list, and complementing with randomly selected potential defects from the merged list.

13. The method of claim 12, wherein the strategy changes between iterations.

14. The method of claim 12, wherein the strategy changes between iterations in accordance with an item selected from at least one of: increasing the number of randomly selected potential defects in advanced iterations relative to earlier iterations, increasing the number of randomly selected potential defects if a number of true defects identified in a previous iteration is below a threshold, increasing the number of randomly selected potential defects if a number of true defects identified in a previous iterations converges, and changing the number of randomly selected potential defects in accordance with type or location distribution of true defects identified in one or more previous iterations.

15. The method of claim 1, wherein assigning the first probabilities or assigning the second probabilities comprises receiving a user indication to assigning higher priority to potential defects at specific areas or of specific classes.

16. The method of claim 1, wherein the object is a wafer or a mask.

17. A system comprising:
a memory; and
a processor, operatively coupled with the memory, to:
  (a) identify a plurality of potential defects, each potential defect of the plurality of potential defects being associated with a potential defect location;
  (b) perform a first clustering of the plurality of potential defects to obtain a first subset and one or more second subsets, the clustering performed in accordance with spatial distances between potential defect locations such that potential defects in the first subset are characterized by higher density in at least one physical area than potential defects in the one or more second subsets;
  (c) assign first probabilities to potential defects in the first subset to be valid defects, the first probabilities being calculated in accordance with a first policy;
  (d) assign second probabilities to potential defects in the one or more second subsets to be valid defects, the second probabilities being calculated in accordance with one or more second policies specifying how to combine at least two second factors associated with potential defect locations;
  (e) select at least one potential defect from the first subset and the one or more second subsets for review by a review tool in accordance with a third policy specifying how to combine potential defects from a plurality of subsets into a merged list, and wherein the selecting of the at least one potential defect for review by the review tool is further in accordance with a strategy indicating how to combine top elements from the merged list and randomly selected elements from the merged list in accordance with a number of reviews from the review tool;
  (f) receive validity or class indications for potential defects in a potential defect lists associated with the selected at least one potential defect, the validity or class indications being received subsequent to potential defects in the potential defect lists being reviewed by the review tool; and
  (g) subsequent to a stopping criteria not being observed:
    (i) update the first, second, or third policy in accordance with validation or classification of an item in the first subset and the one or more second subsets; and
    (ii) repeat steps (c)-(g) in accordance with the first, second, or third policy as updated, until the stopping criteria is observed.

18. The system of claim 17, wherein the stopping criteria is selected from one or more of: a predetermined number of potential defects being reviewed by the review tool, convergence of a number of indications that a potential defect is valid, and a predetermined number of defects associated with a specific defect class being detected.

19. The computerized system of claim 17, wherein to select the at least one potential defect, the processor is further to:
sort potential defects of the first subset according to at least one first probability to obtain a first sorted list;
sort the one or more second subsets according to at least one second probability to obtain a second sorted list;
prioritize potential defects from the first sorted list or the second sorted list to form a merged list in accordance with the third policy; and
select potential defects to be reviewed from the merged list in accordance with the strategy, and wherein the third policy complies with at least one item selected from:
  selecting a predetermined percentage of a required number of potential defects from the first sorted list and complementing with potential defects from the second sorted list;
  selecting top probability potential defects from a merged list of the first sorted list and the second sorted list, sorted by probability; and
  prioritizing potential defects from the first sorted list or the second sorted list in accordance with user input and selecting top priority potential defects.

20. A non-transitory computer readable storage medium retaining program instructions, which when read by a processor, cause the processor to perform operations comprising:
  (a) identifying, by the processor, a plurality of potential defects, each potential defect of the plurality of potential defects being associated with a potential defect location;
  (b) performing, by the processor, a first clustering of the plurality of potential defects to obtain a first subset and one or more second subsets, the clustering performed in accordance with spatial distances between potential defect locations such that potential defects in the first subset are characterized by higher density in at least one physical area than potential defects in the one or more second subsets;
  (c) assigning, by the processor, first probabilities to potential defects in the first subset to be valid defects, the first probabilities being calculated in accordance with a first policy;
  (d) assigning, by the processor, second probabilities to potential defects in the one or more second subsets to be valid defects, the second probabilities being calculated in accordance with one or more second policies specifying how to combine at least two second factors associated with potential defect locations;
  (e) selecting, by the processor, at least one potential defect from the first subset and the one or more second subsets for review by a review tool in accordance with a third policy specifying how to combine potential defects from a plurality of subsets into a merged list, and wherein the selecting of the at least one potential defect for review by the review tool is further in accordance with a strategy indicating how to combine top elements from the merged list and randomly selected elements from the merged list in accordance with a number of reviews from the review tool;

(f) receiving, by the processor, validity or class indications for potential defects in a potential defect lists associated with the selected at least one potential defect, the validity or class indications being received subsequent to potential defects in the potential defect lists being reviewed by the review tool; and (g) subsequent to a stopping criteria not being observed:
  (i) updating, by the processor, the first, second, or third policy in accordance with validation or classification of an item in the first subset and the one or more second subsets; and
  (ii) repeating, by the processor, steps (c)-(g) in accordance with the first, second, or third policy as updated, until the stopping criteria is observed.

* * * * *